(12) United States Patent
Kane et al.

(10) Patent No.: US 6,515,186 B2
(45) Date of Patent: Feb. 4, 2003

(54) PROCESS FOR OBTAINING ALPHA-CAMPHOLENIC ALDEHYDE

(75) Inventors: Bernard J. Kane, Atlantic Beach, FL (US); Gary P. Sanders, Fernandina Beach, FL (US); Joe W. Snow, Jacksonville, FL (US); Mark B. Erman, Atlantic Beach, FL (US)

(73) Assignee: Millennium Specialty Chemicals, Jacksonville, FL (US)

( * ) Notice: Subject to any disclaimer, the term of this patent is extended or adjusted under 35 U.S.C. 154(b) by 0 days.

(21) Appl. No.: 09/850,780

(22) Filed: May 8, 2001

(65) Prior Publication Data

US 2002/0169343 A1 Nov. 14, 2002

(51) Int. Cl.$^7$ .......................... C07C 45/51; C07C 47/40
(52) U.S. Cl. ........................................ 568/443; 568/446
(58) Field of Search ................................. 568/443, 446

(56) References Cited

U.S. PATENT DOCUMENTS 4,052,341 A    10/1977    Naipawer et al.

FOREIGN PATENT DOCUMENTS

WO    WO 00/69777    11/2000

OTHER PUBLICATIONS

Arbusow, B. Studium der Isomerisation von Terpenoxyden. *Berichte der Deutschen Chemischen Gesellschaft* B. II S. 1430–1435 (1935).
Chapius, C. et al. Preparaton of Campholenal Analogues: Chirons for the Lipophilic Moiety of Sandalwood–Like Odorant Alchols. *Helv. Chim. Acta* 75:1527–1546 (1992).
Hölderich, W.F. et al., The use of zeolites in the synthesis of fine and intermediate chemicals. *Catalysis Today* 33:353–366 (1997).
Kaminska, J. et al. The isomerization of α–pinene oxide with Bronsted and Lewis acids. *Rec. Trav. Chim. Pays–Bas* 111:432–437 (1992).
Kunkeler, P.J. et al. Application of zeolite titanium Beta in the rearrangement of α–pinene oxide to campholenic aldehyde. *Catalysis Letters* 53:135–138 (1998).
Naipawer et al. *Chem. Abstr.* 88:22229a (1978).
Vialemaringe, M. et al., 2,3–époxypinane et acides de Lewis: mise au point. *C. R. Acad. Sci. Paris* t. 2, Serie II c, 449–454 (1999).

*Primary Examiner*—Sreeni Padmanabhan
*Assistant Examiner*—Sikarl A. Witherspoon
(74) *Attorney, Agent, or Firm*—Needle & Rosenberg, P.C.

(57) ABSTRACT

A process for obtaining alpha-campholenic aldehyde, which is useful as an aroma chemical and as a synthetic intermediate for other aroma chemicals, particularly those with a sandalwood odor, and also for some pharmaceuticals, is provided. In particular, the invention includes a continuous process for obtaining optically active or racemic α-campholenic aldehyde by a catalytic rearrangement of optically active or racemic α-pinene oxide that can be commercially practicable.

In one embodiment, the method comprises continuously feeding α-pinene oxide to a mixture including catalyst(s) and solvent(s), where the solvent(s) have a boiling point higher than the boiling point of α-campholenic aldehyde, under conditions sufficient to provide for the complete, or at least partial, conversion of α-pinene oxide into α-campholenic aldehyde. The process further includes continuously removing α-campholenic aldehyde from the reaction zone by suitable techniques such as distillation.

18 Claims, 2 Drawing Sheets

PROCESS FOR OBTAINING ALPHA-CAMPHOLENIC ALDEHYDE

FIELD OF THE INVENTION

The invention relates to a process for obtaining alpha-campholenic aldehyde, which is useful as an aroma chemical and as a synthetic intermediate for other aroma chemicals, particularly those with a sandalwood odor, and also for some pharmaceuticals.

BACKGROUND OF THE INVENTION

A practically sound method for obtaining α-campholenic aldehyde was described by B. Arbuzow in 1935 (Berichte der Deutschen Chemischen Gesellschaft, 1935, B.II, S.1430–1435).

According to this article, α-pinene oxide rearranged exothermically in the presence of zinc bromide catalyst in benzene solvent to give about 80% yield of alpha-campholenic aldehyde (Scheme 1). Since then, this batch process, or variations thereof, has been described in numerous publications and patents.

Most of these variations consisted in using different Lewis acids as catalysts, and also different solvents. For instance, zinc chloride in benzene gave a 70% yield of α-campholenic aldehyde (R. I. Naipawer and W. M. Easter, U.S. Pat. No. 4,052,341, 1977; Chem. Abstr. 88: 22229a, 1978). Boron trifluoride etherate in toluene at minus 50° C. gave 73% yield (M. Vialemaringe, et al. C. R. Acad. Sci. Paris, 1999, t. 2, Serie II c, pp. 449–454). A number of Lewis and Bronsted acids and solvents had been examined by J. Kaminska, et al. in: Recl. Trav. Chim. Pays-Bas, 1992, 111, pp. 432–437. Best results were obtained, again, with zinc bromide and zinc chloride.

Scheme 1

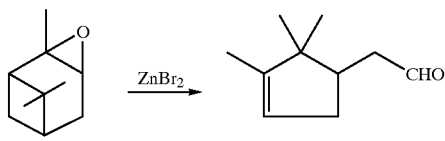

The rearrangement of α-pinene oxide into α-campholenic aldehyde is stereospecific. For example, (−)-α-pinene oxide was converted to (+)-R-α-campholenic aldehyde (Scheme 2, a) in 75% yield in the presence of zinc bromide in refluxing toluene (C. Chapuis and R. Brauchli, Helv. Chim. Acta, 1992, Vol. 75, pp. 1527–1546). Respectively, (+)-α-pinene oxide gives (−)-S-α-campholenic aldehyde (Scheme 2, b).

Scheme 2

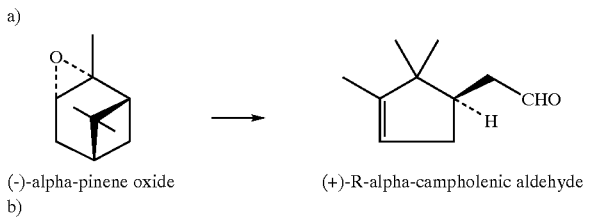

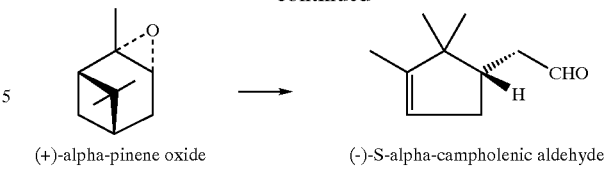

From a practical standpoint, these batch methods for the rearrangement of α-pinene oxide into α-campholenic aldehyde have a series of drawbacks, namely low throughput per unit of equipment volume, and also low turnover numbers in moles of product per mole of catalyst. For instance, in all cited above references the turnover ranges from 20 to 200 moles/mole.

The total turnover can be improved by repeatedly recycling the catalyst as disclosed in WO 00/01793 (P. Davey, et al.). The rearrangement is carried out in toluene in the presence of zinc bromide. After the reaction, zinc bromide is extracted from the mixture with water. This aqueous solution is reused in the next batch reaction after azeotrope removal of the water. Although this procedure can increase the turnover, it is laborious and does not improve the throughput.

Certain heterogeneous catalysts have been employed for the rearrangement of α-pinene oxide into α-campholenic aldehyde. For example, it was reported that a selectivity of about 78% to α-campholenic aldehyde has been achieved in a batch process on highly dealuminated specially pretreated H-US-Y zeolite at 0° C. in toluene solvent. The reaction took 24 hours at catalyst loading 13.3% of the weight of α-pinene oxide. See: W. F. Hölderich, et al. Catalysis Today, 1997, Vol. 33, pp. 353–366.

Zeolite Ti-β has been reported to give a high selectivity towards α-campholenic aldehyde in a gas-phase continuous process at 90° C. However, the throughput in this process was significantly reduced because α-pinene oxide has been fed in the reactor strongly diluted (to 1%) with carrier gas (nitrogen) and n-heptane or dichloroethane as a co-adsorbate in order to decrease the formation of by products. See: P. J. Kunkeler, et al. Catalysis Letters, 1998, Vol. 53, pp. 135–138.

Therefore, the need still exists for a continuous and yet commercially practical technique for the rearrangement of α-pinene oxide into α-campholenic aldehyde.

SUMMARY OF THE INVENTION

Among other aspects, the present invention is based on the surprising discovery that a continuous process for obtaining optically active or racemic α-campholenic aldehyde by a catalytic rearrangement of optically active or racemic α-pinene oxide can also be commerically practicable.

In one embodiment, the method comprises continuously feeding α-pinene oxide to a mixture including catalyst(s) and solvent(s), where the solvent(s) have a boiling point higher than the boiling point of α-campholenic aldehyde, under conditions sufficient to provide for the complete, or at least partial, conversion of α-pinene oxide into α-campholenic aldehyde. The process further includes continuously removing α-campholenic aldehyde from the reaction zone by suitable techniques such as distillation.

1 is a 5-liter three-neck flask.
2—circulation tube, here a ½ inch stainless steel optionally heated with an electrical tape.
3—circulation pump (gear type).
4—electrically heated 26×¾ inch stainless steel tube (reactor).
5—circulation tube, here a ½ inch stainless steel tube, optionally electrically heated.
6—feed pump (gear type)/feed tube.
7—Vigreux column, 12×1.5 inch.
8—distillation head.
9—condenser.
10—vacuum-adapter.
11—vacuum-adapter.
12. 5-liter receiver.
13—drain valve; and
TC—thermocouples.

Figure 2:
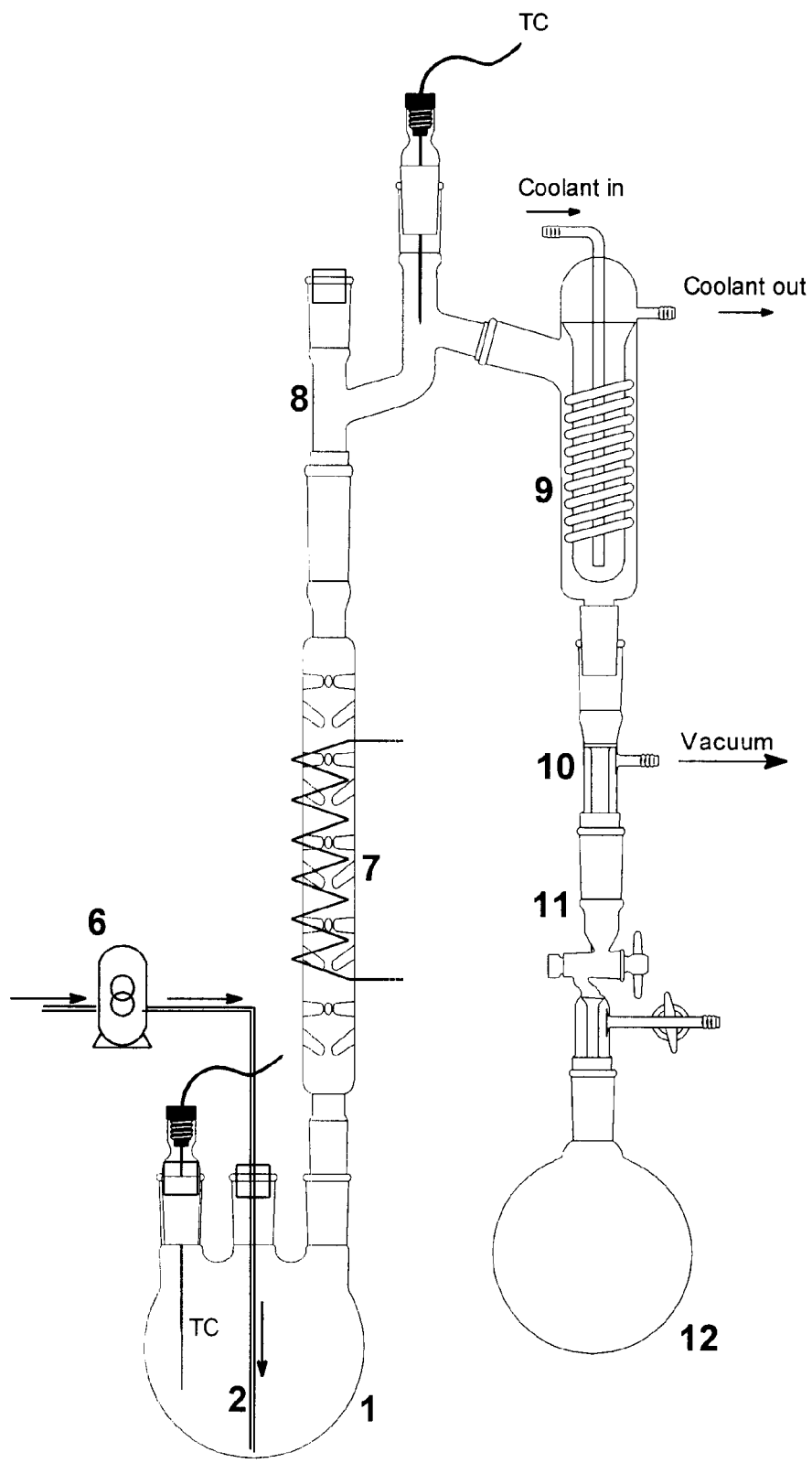

FIG. 2 represents another suitable laboratory setup wherein α-pinene oxide is fed to the bottom of the distillation flask under the layer of the reaction mixture. In this example, the reference numerals define the same components or components having the same function. For example:

1 is a 5-liter three-neck flask.
6—feed pump (gear type)/feed tube, here, a ⅛ inch stainless steel feed tube.
7—Vigreux column, 12×1.5 inch.
8—distillation head.
9—condenser.
10—vacuum-adapter.
11—vacuum-adapter.
12. 5-liter receiver.
TC—thermocouples.

DETAILED DESCRIPTION OF PREFERRED EMBODIMENTS

The present invention may be understood more readily by reference to the following detailed description of certain preferred embodiments of the invention and the Examples included therein.

As used in the specification and the appended claims, the singular forms "a", "an", and "the" include plural referents unless the context clearly dictates otherwise. Thus, for example, reference to "a catalyst" includes mixtures of two or more catalysts, reference to "a solvent" includes mixtures of two or more solvents, and the like.

Ranges are often expressed herein as from "about" one particular value to "about" another particular value. When such a range is expressed, another embodiment includes from the one particular value to the other particular value. Similarly, when values are expressed as approximations, by use of the antecedent "about", it will be understood that the particular value forms another embodiment.

One aspect of the present invention relates to a continuous method for obtaining α-campholenic aldehyde, in its racemic or optically active form, by the catalytic rearrangement of α-pinene oxide, in its racemic or optically active form.

More specifically, the process of the present invention includes continuously introducing α-pinene oxide into a reaction mixture and removing α-campholenic aldehyde from the reaction mixture by suitable techniques, e.g., vacuum-distillation. Such a process can be capable of providing higher throughput and yield of the product.

The alpha-pinene oxide is well known in the art and need not be described in detail here.

The process of the present invention includes introducing alpha-pinene oxide into a reaction mixture that includes both one or more catalysts and one or more solvents. The mixture can be in a suitable form, e.g., a solution, a suspension or dispersion of the catalyst(s) in the solvent(s).

As discussed above, one component of the reaction mixture is at least one catalyst.

The catalysts can be chosen from among those substances capable of effecting the rearrangement of α-pinene oxide into α-campholenic aldehyde.

In this regard, the catalysts can be homogeneous catalysts and/or heterogeneous catalysts.

Examples of suitable catalysts include acids, with specific examples of such catalysts including Lewis acids, particularly zinc bromide and zinc chloride.

Another component of the reaction mixture is at least one solvent.

The solvent(s) preferably employed in this invention are those solvents having a boiling point higher than the boiling point of α-campholenic aldehyde.

The solvents, in this regard, can include organic solvents of all classes.

Specific examples of preferred solvents are aliphatic, alicyclic, and aromatic hydrocarbons, esters, ethers, glycols, glycol ethers, glycol esters, glycol oligomers, ethers and esters of glycol oligomers, polyglycols, ethers and esters of polyglycols, chloroalkanes, chloroalkenes, bromoalkanes, bromoalkenes, chloroarenes, bromoarenes, substituted amines, amides, and nitriles. Obviously, a solvent can contain several similar or different functional groups.

Other components that may optionally be present in the reaction mixture include mineral oils.

The concentration of the catalyst in the reaction mixture solvent can vary in a road range depending on the specific choice of catalyst(s) and solvent(s). The referred concentration of the catalyst can range from about 0.001 mole/l as a minimum with about 10 moles/l being a preferred maximum. A more preferred minimum concentration of the catalyst is from about 0.03 mole/l with a more preferred maximum being about 0.5 mole/l.

The reaction mixture can be prepared by generally known methods, which need not be described in detail here.

However, in preparing the reaction mixture, it is sometimes advantageous to use one or more co-solvents, or one or more accessory solvents to facilitate the dissolving of the catalyst(s) in the main or primary solvent(s).

In one embodiment involving accessory solvent(s), the accessory solvents have boiling points lower than the boiling point of α-campholenic aldehyde, and can be removed in the early stages of the process by distillation.

Examples of such accessory solvents include, but are not limited to lower alcohols: methanol, ethanol, n-propanol, isopropanol, butanol, and hexanol.

Alternatively, the accessory solvent(s) can have a higher boiling point than that of α-campholenic aldehyde, or even a higher boiling point than the boiling point of the main, or primary, solvent.

Examples of these accessory solvents include, but are not limited to alcohols, ethers, esters, nitrites, amides, nitroalkanes, nitroarenes, glycols, glycol ethers, glycol oligomers, ethers of glycol oligomers, polyglycols, ethers of polyglycols. Examples of suitable accessory solvents include, but are not limited to: methanol, ethanol, isopropanol, n-hexanol, n-dodecanol, acetonitrile, dibutyl ether of diethylene glycol, dimethyl ether of tetraethylene glycol, etc.

The reaction mixture is present in, and/or circulated through at least one zone which zone can be associated with a single function or more than one function. For example, the zone can be a reaction zone that can be heated to a desired temperature, and/or an evaporation zone that can be in fluid communication with a desired separation device.

Figure 1:
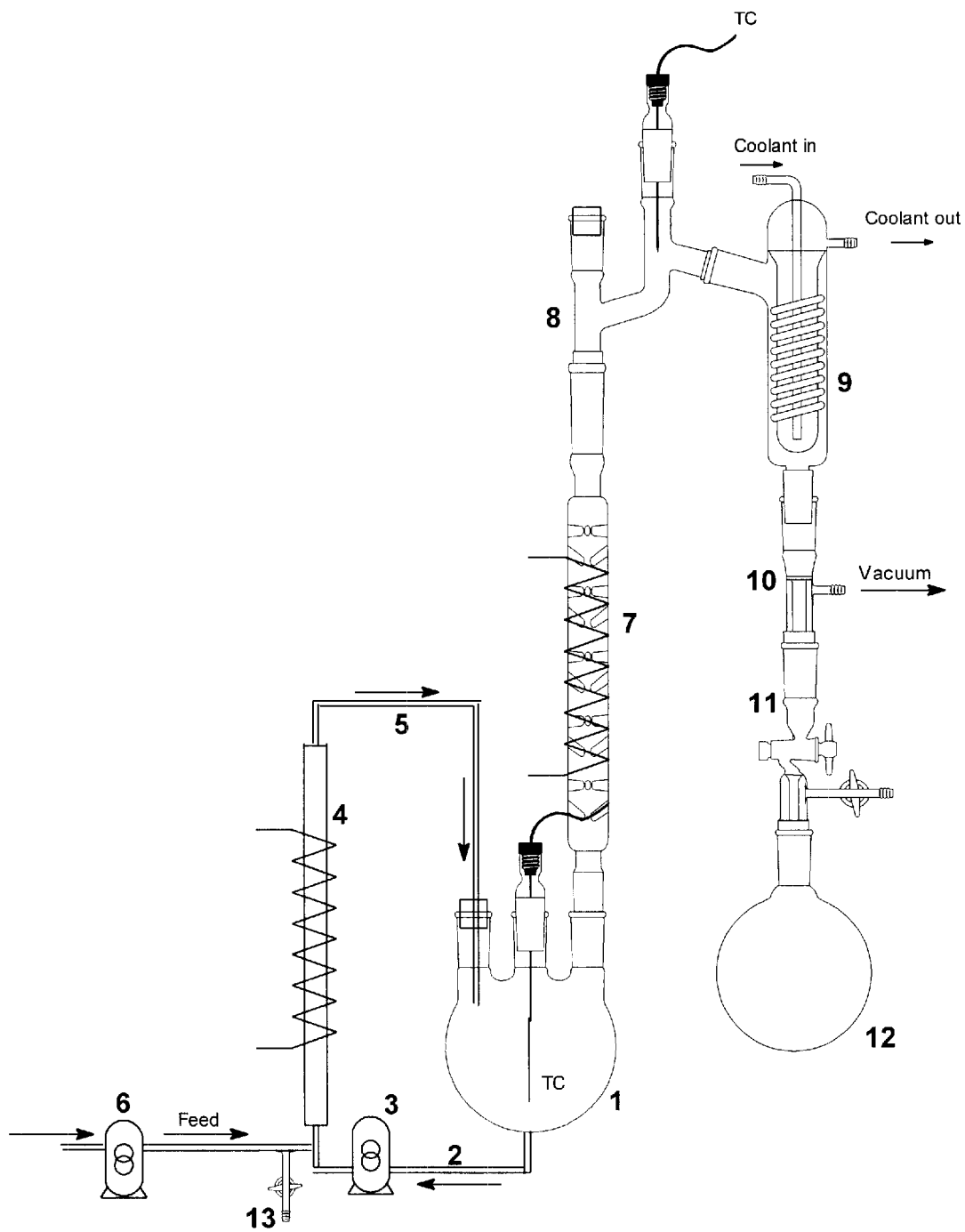
FIG. 1 represents one example of a laboratory setup, according to the invention, wherein α-pinene oxide is fed into a heated circulation loop (reactor). In this figure.

For example, this invention can employ a single zone as shown in FIG. 2, which serves as both an evaporation zone and a reaction zone, or more than one zone, such as that of FIG. 1, where a reaction zone includes an evaporation zone, and an additional zone which is external to an evaporation zone, but is in fluid communication with the evaporation zone. In systems such as that of FIG. 2, the evaporation zone can also act as a reaction zone.

The zones of the inventive process can be provided by any device recognized in the art to provide the desired function. For example, the zone that provides for the desired reaction and evaporation functions can be a distillation vessel, e.g., distillation flask or other suitable device. Similarly, an external reaction zone present in a circulation loop that does not seek to provide the evaporation function can be a tubular reactor (as illustrated at 4 in FIG. 1) or any other shape reactor.

As discussed above, the inventive process is a process that involves both the rearrangement of alpha-pinene oxide into the aldehyde and the removal of the aldehyde product from the reaction mixture.

A first aspect of the process involves rearrangement of the oxide. Broadly speaking, alpha-pinene oxide is rearranged under reaction conditions suitable to provide for rearrangement of at least a portion of the oxide into alpha-campholenic aldehyde.

Because α-pinene oxide has a boiling point lower than the boiling point of the product α-campholenic aldehyde, the rate of reaction is important. That is, when α-pinene oxide does not react sufficiently fast, it can distill off of the reaction mixture before the product α-campholenic aldehyde forms, and in such cases the process cannot be efficient. Therefore, the reaction conditions of the process are preferably sufficient to provide a complete or almost complete conversion of α-pinene oxide.

By "almost complete" conversion, it is meant that only a minor amount, typically no more than 10%, of starting α-pinene oxide remains unreacted.

A second aspect of the inventive process involves removal of the desired aldehyde product from the reaction mixture.

In view of the differences in boiling point between the product and the solvent, separation techniques that are based on such differences, e.g, distillation techniques, are preferred.

Suitable distillation techniques are well recognized in the art and as such, need not be described in detail here. However, it is worth noting that the inventive process can employ any distillation device or apparatus that is recognized in the art.

For example, the removal of the product from the reaction mixture via distillation can be preferably performed by either vacuum distillation or under atmospheric pressure. The vacuum is selected depending on the temperature in the distillation vessel, and vice versa. The preferred pressure is typically within the range of 0.1 Torr. to 760 Torr. A more preferred pressure is from about 5 Torr. to about 50 Torr.

Optimization of the process can involve the optimization of either, or preferably both, of the rearrangement and removal steps. Moreover, optimization can involve a variety of reaction conditions, including temperature, pressure, feed and removal rate among others.

The balance of this description will focus on optimization of the preferred embodiments employing distillation as the aldehyde removal technique.

The reaction temperature is typically selected so as to maintain both a sufficient reaction rate and a distillation rate of the product α-campholenic aldehyde.

It is also advantageous, although not necessary, to maintain a near steady level of reaction mixture in the system. This can be accomplished, for example, by maintaining a distillation rate that is about equal to the feed rate.

In certain cases, especially at high throughputs, some quantities of the main solvent(s) can be removed from the system, e.g., distilled or carried over with the product α-campholenic aldehyde. In such cases, it may be advantageous to co-feed some quantities of the solvent(s) together with α-pinene oxide, in order to maintain about permanent level of solvent in the system.

In addition to selection of suitable catalyst(s) and its concentration, main solvent(s) and accessory solvent(s) for the reaction mixture, reaction temperature, feed rate and distillation rate, and pressure (vacuum), this process can typically be optimized by the contact time of α-pinene oxide with the reaction mixture.

Contact time can depend on the design of the reaction system, and in particular, the point of introduction of α-pinene oxide into the system.

The reaction mixture is present in the zone, with the precise function of the zone being dependent on the overall nature of the reaction system. In order to better illustrate this aspect of the invention, the invention will now be discussed in terms of two examples of suitable reaction systems—FIGS. 1 and 2. In each case, the zone is illustrated as a distillation vessel in communication with the distillation column. However, these reaction systems are only illustrative and in no way limitative.

In a system having a single reaction zone, e.g., where the distillation vessel 1 is both an evaporation zone and the reaction zone, such as illustrated by FIG. 2, it can be advantageous to feed α-pinene oxide under the surface of the reaction mixture in the reaction zone. In this case, α-pinene oxide has sufficient time to react to provide the desired product.

The optimum depth of the feed point under the surface depends on the size of the reactor and on a number of other parameters, and can be found experimentally. For example, in a 5-liter reactor shown on FIG. 2, with initial charge of the solvent-catalyst mixture of about 1 liter, good results were obtained by feeding α-pinene oxide to the bottom of the reactor (see Example 2).

Generally, the temperature is selected from the range between plus 40° C. and plus 210° C. in the distillation vessel 1.

Another example of a suitable, and often preferred system, provides for circulation of the reaction mixture. Such a process can be illustrated by the reaction set up as shown on FIG. 1.

In this version, the reaction mixture is present in the zone shown as distillation flask 1 that acts as an evaporation/reaction zone, however, the system includes one or more additional reaction zones. For example, the reaction mixture can be circulated through the distillation flask 1 and an optionally heated reaction zone 4, while the α-pinene oxide is fed in the circulation loop, preferably at a point before the reaction zone 4. In such setup, it can be easier to find the parameters that provide the optimum contact time, by varying not only the feed rate, but also the rate of circulation.

The reaction system can affect other parameters such as reaction temperature. For example, in a setup with an external reaction zone like the one shown on FIG. 1, the actual temperature in the reaction zone can be significantly higher (up to plus 400° C.) than that associated with FIG. 2. The preferred temperature range in the reaction zone is from about plus 50° C. to about 190° C. A more preferred temperature in the reaction zone is from about 70° C. to about 120° C. It is to be understood that the temperature may not be uniform throughout the reaction zone(s).

It is to be understood, however, that the two experimental setups shown on FIG. 1 and FIG. 2 are given here for illustrative and explanatory purposes only, and in no way limit the invention.

As can be seen, numerous other useful designs can be realized according to the invention. For example, in certain designs, the reaction zone may include both the distillation vessel and the circulation loop. In other, simpler designs like the one shown on FIG. 2, the distillation vessel is the reaction zone.

In addition, individual elements employed in the system may also vary. For example, suitable devices such as a falling film evaporator can be used instead of a distillation vessel shown on FIG. 1 for a design with an external reaction zone.

Alternatively, the process itself can be varied. As an example of the ability to vary the inventive process, a solution of the catalyst can be added to the reactor continuously. At the same time, about equal amount of the contents of the reactor can be pumped out to maintain an about permanent level of the mixture in the reaction system.

The process of the present invention is capable of providing a more convenient and practical process for obtaining α-campholenic aldehyde from α-pinene oxide. The method is also environmentally benign because it provides for reduced amounts of waste catalysts and solvents per weight unit of the product.

The advantages that can be associated with the invention may be realized and attained by means of the elements and combinations particularly pointed out in the claims. It is to be understood that both the foregoing description of the invention and the following examples are not restrictive to the invention, as claimed.

EXAMPLES

The following examples are put forth so as to provide those of ordinary skill in the art with a complete disclosure and description of how the method for obtaining α-campholenic aldehyde is realized, and are intended to be purely exemplary of the invention and are not intended to limit the scope of what the inventors regard as their invention. Efforts have been made to ensure accuracy with respect to numbers (e.g. amounts, temperature, etc.) but some errors and deviations may be present.

Example 1

Continuous Rearrangement of α-Pinene Oxide into α-Campholenic Aldehyde in Diphenyl Ether as a Higher Boiling Solvent and n-Hexanol as an Accessory Solvent for the Catalyst Diphenyl ether (1000 g) and a solution of 24 g (0.1066 mole) of zinc bromide in 51 g of n-hexanol was charged in the reactor shown on FIG. 1 (in the 5-liter flask 1). Circulation pump 3 was turned on and the circulation rate was established at about 750 ml per minute. The system was evacuated to 9±1 Torr., and such pressure was maintained throughout the whole process. Heat was applied to the circulation loop (reactor 4 and stainless steel pipe 5) to maintain temperature 105° C. in the flask 5 throughout the whole process. Coolant (water-ethylene glycol mixture) at plus 5° C. was passed through condenser 9. After the temperature in the flask 5 stabilized at the required 105° C., a mixture of 90% by weight of α-pinene oxide and 10% by weight of diphenyl ether was continuously fed in the connection pipe between circulation pump 3 and reactor 4 at a rate of about 2.1 g per minute. In several minutes, the product α-campholenic aldehyde started continuously distilling into the receiver 12 at a rate about equal to the feed rate of 2.1 g per minute. An accessory moderate heat was applied to the Vigreux column to facilitate the distillation. The temperature in the distillation head 8 during the process varied within the range of from about 75° C. to about 85° C. During the process, composition of the distillate was periodically monitored by GLC. In addition to the product α-campholenic aldehyde, the initial fractions of the distillate contained some co-solvent hexanol, and all fractions contained more or less diphenyl ether (usually about 10–12%). The analysis of the distillate fractions showed that conversion of α-pinene oxide into α-campholenic aldehyde was complete or almost complete during first 273 hours of the process. Then, concentration of unreacted α-pinene oxide in the distillate started slowly growing, and the process was discontinued when this concentration reached 10%. Total process time 415 hours. Total amount of 98% α-pinene oxide fed was 46.91 kg (302 moles). Total amount of the distillate obtained was 50.66 kg, with an average weighed concentration of α-campholenic aldehyde of 72.86%, and an average weighed concentration of α-pinene oxide 2.84%. Based on this data, total yield of α-campholenic aldehyde was 36.91 kg (242.5 moles). Yield of α-campholenic aldehyde—80.3% of the theory. Turnover number—2275.

Example 2

Continuous Rearrangement of α-Pinene Oxide into α-Campholenic Aldehyde in Diphenyl Ether as a Higher Boiling Solvent and n-Hexanol as an Accessory Solvent for the Catalyst The process was carried out as in example 1, with the exception that the feed rate was 4.33 g/min. Total process time 136 hours. Total amount of 98% α-pinene oxide fed was 31.70 kg (204 moles). Total amount of the distillate obtained was 34.45 kg, with an average weighed concentration of α-campholenic aldehyde of 73.12%. Based on this data, total yield of α-campholenic aldehyde was 25.19 kg (165.5) moles. Yield of α-campholenic aldehyde—81.1% of the theory. Turnover number—1553.

Example 3

Continuous Rearrangement of α-Pinene Oxide into α-Campholenic Aldehyde in Diphenyl Ether as a Higher Boiling Solvent and n-Hexanol as an Accessory Solvent for the Catalyst The process was carried out as in example 1, with the exception that the feed rate was 8.96 g/min. Total process time 40.5 hours. Total amount of 98% α-pinene oxide fed was 17.46 kg (112 moles). Total amount of the distillate obtained was 19.13 kg, with an average weighed concentration of α-campholenic aldehyde of 71.72%. Based on this data, total yield of α-campholenic aldehyde was 13.72 kg (90.1 moles). Yield of α-campholenic aldehyde—80.4% of the theory. Turnover number—845.

Example 4

Continuous Rearrangement of α-Pinene Oxide into α-Campholenic Aldehyde in Diphenyl Ether as a Higher Boiling Solvent and Ethanol as an Accessory Solvent for the Catalyst Diphenyl ether (1000 g) and a solution of 14.4 g (0.064 mole) of zinc bromide in 60.6 g of ethanol was charged in the reactor shown on FIG. 1 (in the 5-liter flask 1). Circulation pump 3 was turned on and the circulation rate was established at about 750 ml per minute. The system was evacuated to 9±1 Torr., and such pressure was maintained throughout the whole process. Heat was applied to the circulation loop (reactor 4 and stainless steel pipe 5) to maintain temperature 105° C. in the flask 5 throughout the whole process. Coolant (water-ethylene glycol mixture) at plus 5° C. was passed through condenser 9. After the temperature in the flask 5 stabilized at the required 105° C., a mixture of 80% by weight of α-pinene oxide and 20% by weight of diphenyl ether was continuously fed in the connection pipe between circulation pump 3 and reactor 4 at a rate of about 4.5 g per minute. In several minutes, the product α-campholenic aldehyde started continuously distilling into the receiver 12 at a rate about equal to the feed rate of 4.5 g per minute. An accessory moderate heat was applied to the Vigreux column to facilitate the distillation. The temperature in the distillation head 8 during the process varied within the range of from about 75° C. to about 95° C. During the process, composition of the distillate was periodically monitored by GLC. In addition to the product α-campholenic aldehyde, all fractions contained more or less diphenyl ether (usually about 20%). Total process time was 83 hours, then it was discontinued. The analysis of the distillate fractions showed that conversion of α-pinene oxide into α-campholenic aldehyde was complete or almost complete during the whole process. Total amount of 97.3% α-pinene oxide fed was 17.94 kg (17.46 kg of 100-%; 114.7 moles). Total amount of the distillate obtained was 21.20 kg, with an average weighed concentration of α-campholenic aldehyde of 68.50%, and an average concentration of α-pinene oxide 0.12–0.13%. Based on this data, total yield of α-campholenic aldehyde was 14.52 kg (95.4 moles). Yield of α-campholenic aldehyde—83.2% of the theory. Turnover number—1491.

Example 5

Continuous Rearrangement of α-Pinene Oxide into α-Campholenic Aldehyde in Diethylene Glycol Dibutyl Ether as a Higher Boiling Solvent and n-Hexanol as an Accessory Solvent for the Catalyst The process was carried out as in example 1, with the exception that 500 g of diethylene glycol dibutyl ether was substituted for 1 kg of diphenyl ether. Total process time 47 hours. Total amount of 98% α-pinene oxide fed was 5.60 kg (36.05 moles). Total amount of the distillate obtained was 4.94 kg, with an average weighed concentration of α-campholenic aldehyde of 77.5%. Based on this data, total yield of α-campholenic aldehyde was 3.83 kg (25.2) moles. Yield of α-campholenic aldehyde—69.9% of the theory. Turnover number—236.

Example 6

Continuous Rearrangement of α-Pinene Oxide into α-Campholenic Aldehyde in n-Butyl Benzoate Zinc bromide (24 g, 0.1066 mole) was dissolved in 1000 g of n-butyl benzoate, and the resulting solution was charged in the reactor shown on FIG. 1 (in the 5-liter flask 1). Then, the reaction was carried out as in example 1, with the exception that the feed consisted of 98% purity α-pinene oxide, without a compensatory solvent.

Example 7

Continuous Rearrangement of α-Pinene Oxide into α-Campholenic Aldehyde in Diphenyl Ether as a Higher Boiling Solvent and n-Hexanol as Accessory Solvent for the Catalyst Diphenyl ether (1000 g) and a solution of 24 g (0.10658 mole) of zinc bromide in 51 g of n-hexanol was charged in the reactor shown on FIG. 2 (in the 5-liter flask 1). The system was evacuated to 9±1 Torr., and such pressure was maintained throughout the whole process. The mixture was heated to 105° C. in the flask 5, and this temperature was maintained throughout the whole process. Coolant (water-ethylene glycol mixture) at plus 5° C. was passed through condenser 9. After the temperature in the flask 5 stabilized at the required 105° C., a mixture of 93% by weight of α-pinene oxide and 7% by weight of diphenyl ether was continuously fed to the bottom of the flask 5 through a feed tube from pump 6' at a rate of about 8.6 g per minute. In several minutes, the product α-campholenic aldehyde started continuously distilling into the receiver 12 at a rate about equal to the feed rate of 8.6 g per minute. An accessory moderate heat was applied to the Vigreux column to facilitate the distillation. The temperature in the distillation head 8 during the process varied within the range of from about 75° C. to about 93° C. During the process, composition of the distillate was periodically monitored by GLC. In addition to the product α-campholenic aldehyde, the initial fractions of the distillate contained some co-solvent hexanol, and all fractions contained more or less diphenyl ether (usually about 10–12%). Total process time 62 hours. Total amount of 98% α-pinene oxide fed was 28.1 kg (180.9 moles). Total amount of the distillate obtained was 29.67 kg, with an average weighed concentration of α-campholenic aldehyde of 72.30%. Based on this data, total yield of α-campholenic aldehyde was 21.45 kg (140.9 moles). Yield of α-campholenic aldehyde—77.9% of the theory. Turnover number—1322.

We claim:

1. A process for producing optically active or racemic alpha-campholenic aldehyde by a catalytic rearrangement of optically active or racemic alpha-pinene oxide comprising:

(i) providing a zone containing a mixture comprising at least one catalyst and at least one solvent, wherein the catalyst is a catalyst suitable for effecting conversion of alpha-pinene oxide into alpha-campholenic aldehyde and the solvent has a boiling point higher than the boiling point of alpha-campholenic aldehyde, (ii) continuously feeding alpha-pinene oxide to the mixture under conditions sufficient to convert at least a portion of the alpha-pinene oxide into alpha-campholenic aldehyde, and (iii) continuously removing alpha-campholenic aldehyde from the zone through distillation.

2. The process of claim 1 wherein alpha-pinene oxide is fed under the surface of the mixture in the zone.

3. The process of claim 1 wherein the zone is a heated reaction zone and step (ii) comprises introducing alpha-pinene oxide into the heated reaction zone.

4. The process of claim 3 wherein alpha-pinene oxide is fed under the surface of the mixture in the heated reaction zone.

5. The process of claim 1 wherein the zone is an evaporation zone which is in fluid communication with a circulation loop, which loop includes a heated reaction zone, wherein step (ii) comprises introducing alpha-pinene oxide into the circulation loop and circulating the mixture in the circulation loop.

6. The process of claim 5 wherein the evaporation zone is a distillation stillpot.

7. The process of claim 5 wherein alpha-pinene oxide is introduced into the heated reaction zone.

8. The process of claim 1 wherein the mixture of catalyst and solvent is circulated through a circulation loop, which includes a distillation stillpot, or any other type evaporator, and an optionally heated reaction zone, which is external with respect to the distillation stillpot or any other type evaporator.

9. The process of claim 8 wherein alpha-pinene oxide is introduced into the optionally heated reaction zone, or any other part of the circulation loop, which is external with respect to the distillation stillpot or any other type evaporator.

10. The process of claim 1 wherein the catalyst is zinc bromide, or zinc chloride, or a mixture thereof.

11. The process of claim 1 wherein the solvent is selected from a group containing aliphatic, alicyclic, and aromatic hydrocarbons, esters, ethers, glycols, glycol ethers, glycol esters, glycol oligomers, ethers and esters of glycol olygomers, polyglycols, ethers and esters of polyglycols, chloroalkanes, chloroalkenes, bromoalkanes, bromoalkenes, chloroarenes, bromoarenes, substituted amines, amides, and nitriles, and mixtures thereof.

12. The process of claim 1 wherein the solvent is diphenyl ether.

13. The process of claim 1 wherein the mixture of step (i) is prepared by using an accessory solvent which accessory solvent dissolves the catalyst more easily than the solvent.

14. The process of claim 13 wherein the accessory solvent is selected from a group containing alcohols, ethers, esters, nitrites, amides, nitroalkanes, nitroarenes, glycols, glycol ethers, glycol oligomers, ethers of glycol oligomers, polyglycols, ethers of polyglycols, or mixtures thereof.

15. The process of claim 1 wherein step (ii) occurs at elevated temperatures.

16. The process of claim 1 wherein the reaction temperature of step (ii) is from about plus 50° C. to about plus 190° C.

17. The process of claim 1 wherein the reaction temperature of step (ii) is from about plus 70° C. to about plus 120° C.

18. The process of claim 1 wherein the concentration of the catalyst in the mixture is from about 0.001 mole/l to about 0.5 mole/l.

* * * * *